(12) United States Patent
Abe et al.

(10) Patent No.: US 7,759,030 B2
(45) Date of Patent: Jul. 20, 2010

(54) P-TERPHENYL COMPOUND AND PHOTOSENSITIVE BODY FOR ELECTROPHOTOGRAPHY USING SUCH COMPOUND

(75) Inventors: Katsumi Abe, Fukushima (JP); Atsushi Takesue, Fukushima (JP); Shinya Nagai, Fukushima (JP); Mitsutoshi Anzai, Kanagawa (JP)

(73) Assignee: Hodogaya Chemical Co., Ltd., Kawasaki-shi (JP)

( * ) Notice: Subject to any disclaimer, the term of this patent is extended or adjusted under 35 U.S.C. 154(b) by 0 days.

(21) Appl. No.: 12/569,012

(22) Filed: Sep. 29, 2009

(65) Prior Publication Data
US 2010/0015542 A1    Jan. 21, 2010

Related U.S. Application Data

(62) Division of application No. 11/597,657, filed as application No. PCT/JP2005/009829 on May 24, 2005.

(51) Int. Cl.
*G03G 15/02* (2006.01)
(52) U.S. Cl. .................... 430/58.35; 564/434
(58) Field of Classification Search .............. 430/58.35; 564/434
See application file for complete search history.

(56) References Cited

U.S. PATENT DOCUMENTS

2009/0053633 A1    2/2009    Nagai et al.

FOREIGN PATENT DOCUMENTS

| EP | 0 314 195 | 5/1989 |
| EP | 1 816 522 A1 | 8/2007 |
| EP | 1 818 725 A1 | 8/2007 |
| JP | 1 118141 | 5/1989 |
| JP | 9 316038 | 12/1997 |
| JP | 10 17531 | 1/1998 |
| JP | 2001 305764 | 11/2001 |
| JP | 2002 117982 | 4/2002 |
| JP | 2003 21921 | 1/2003 |

*Primary Examiner*—Mark A Chapman
(74) *Attorney, Agent, or Firm*—Oblon, Spivak, McClelland, Maier & Neustadt, L.L.P.

(57) ABSTRACT

The present invention provides p-terphenyl compounds represented by the following general formula (1) and (2):

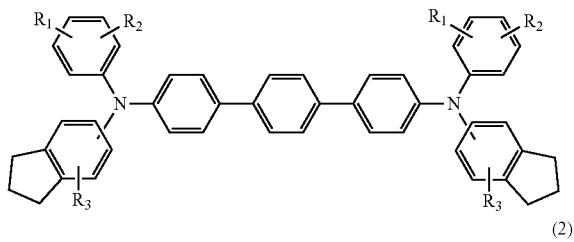

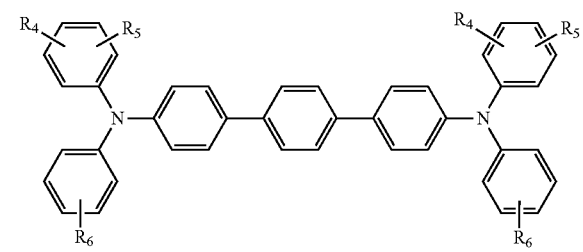

and an electrophotographic photoconductor containing the compound. According to the invention, a charge transporting agent having improved solubility in an organic solvent and an electrophotographic photoconductor excellent in drift mobility and having high sensitivity and high durability are provided.

3 Claims, 8 Drawing Sheets

P-TERPHENYL COMPOUND AND PHOTOSENSITIVE BODY FOR ELECTROPHOTOGRAPHY USING SUCH COMPOUND

This application is a divisional of application Ser. No. 11/597,657, filed Nov. 24, 2006.

TECHNICAL FIELD

The present invention relates to a p-terphenyl compound having improved solubility in an organic solvent and useful as a charge transporting agent used in an electrophotographic photoconductor, and an electrophotographic photoconductor using the same.

BACKGROUND ART

The electrophotographic system is a type of image forming method in which generally, a surface of a photoconductor using a photoconductive material is charged, for example, by corona discharge in a dark place, exposure is performed thereto, the charge of an exposed portion is selectively allowed to dissipate to obtain an electrostatic latent image, and development is performed thereto using a toner, followed by transferring and fixing to paper or the like to obtain an image. An inorganic photoconductive material such as selenium, zinc oxide, cadmium sulfide or silicon has hitherto been widely used as an electrophotographic photoconductor. These inorganic materials have many merits and also have various demerits at the same time. For example, selenium has the disadvantages of requiring hard production conditions and of easily crystallizing by heat or a mechanical impact. Zinc oxide and cadmium sulfide have problems in moisture resistance and mechanical strength, and have the disadvantage in that deterioration of charging and exposure occurs by a dye added as a sensitizer, resulting in lacking in durability. Silicon also requires hard production conditions and is high in cost because a stimulative gas is used, and care must be taken in handling because it is sensitive to humidity. Further, selenium and cadmium sulfide also have the problem of toxicity.

Organic photoconductors using various organic compounds improved in the disadvantages of these inorganic photoconductors have been widely used. The organic photoconductors include a monolayer type photoconductor having a charge generating agent and a charge transporting agent dispersed in a binder resin and a laminate type photoconductor having a charge generating layer and a charge transporting layer functionally separated. The functionally separated type photoconductor has a wide option for each material, and a photoconductor having optional performance can be relatively easily prepared by combination, so that it has been widely used.

As the charge generating agents, many organic pigments and dyes such as an azo compound, a bisazo compound, a trisazo compound, a tetrakisazo compound, a thiapyrylium salt, a squarilium salt, an azurenium salt, a cyanine dye, a perylene compound, a non-metal or metal phthalocyanine compound, a polycyclic quinone compound, a thioindigo-based compound and a quinacridone-based compound have been proposed and put into practical use.

As the charge transporting agents, there are, for example, an oxadiazole compound (patent document 1), an oxazole compound (patent document 2), a pyrazoline compound (patent document 3), a hydrazone compound (patent documents 4 to 7), a diamine compound (patent document 8), a stilbene compound (patent documents 9 to 11), a butadiene compound (patent document 12) and the like. Organic photoconductors using these charge transporting agents have excellent characteristics, and some of them have been in practical use. However, no one sufficiently satisfying various characteristics required for photoconductors of the electrophotographic system has not been obtained yet under the present situation. Further, some are not put in practical use because of their poor compatibility with a resin or their poor solubility in a solvent, although various characteristics such as sensitivity are satisfactory.

In some patent documents published in the past, p-terphenyl compounds are used for applications of electrophotographic photoconductors. In patent document 13, compounds such as p-terphenyl compounds are disclosed, but these are contained in a charge generating layer of a laminate type photoconductor, thereby intending to improve electrophotographic characteristics such as durability and sensitivity. Further, p-terphenyl compounds disclosed in patent document 14 are excellent in solubility, but insufficient in various characteristics such as durability.

Patent Document 1: JP-B-34-5466
Patent Document 2: JP-A-56-123544
Patent Document 3: JP-B-52-41880
Patent Document 4: JP-B-55-42380
Patent Document 5: JP-B-61-40104
Patent Document 6: JP-B-62-35673
Patent Document 7: JP-B-63-35976
Patent Document 8: JP-B-58-32372
Patent Document 9: JP-B-63-18738
Patent Document 10: JP-B-63-19867
Patent Document 11: JP-B-3-39306
Patent Document 12: JP-A-62-30255
Patent Document 13: JP-A-61-129648
Patent Document 14: JP-B-6-73018

DISCLOSURE OF THE INVENTION

A charge transporting agent used in an organic photoconductor requires chemical stability resisting light, ozone and an electric load, and stability and durability that sensitivity does not decrease even by repeated use or long-term use, as well as to satisfy electric characteristics as the photoconductor including sensitivity. Further, when the organic photoconductor is produced, high and stable solubility in a solvent is necessary.

An object of the invention is to provide a p-terphenyl compound useful as a charge transporting agent which has improved solubility in an organic solvent and can realize an electrophotographic photoconductor satisfying photoconductor characteristics and having high sensitivity and high durability, and an electrophotographic photoconductor using the same.

The invention provides a p-terphenyl compound represented by the following general formula (1):

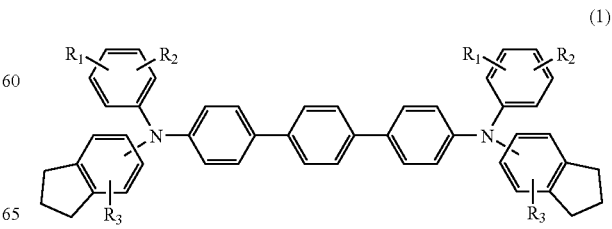

wherein R1, R2 and R3, which may be the same or different, represent a hydrogen atom, an alkyl group, an alkoxy group, an aralkyl group, a halogen atom, a disubstituted amino group or a substituted or unsubstituted phenyl group, and R1 and R2 may form a ring in combination.

Further, the invention provides a p-terphenyl compound represented by the following general formula (2):

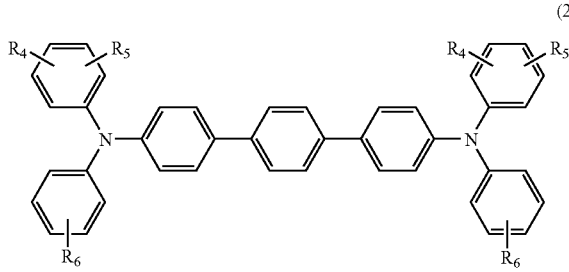

(2)

wherein R4 and R5, which are different from each other, represent an alkyl group, an alkoxy group, an aralkyl group, a halogen atom, a disubstituted amino group or a substituted or unsubstituted phenyl group, and R6 represents a hydrogen atom, an alkyl group, an alkoxy group, an aralkyl group, a halogen atom, a disubstituted amino group or a substituted or unsubstituted phenyl group.

The invention further provides an electrophotographic photoconductor comprising on an electroconductive support one or more p-terphenyl compounds represented by the following general formula (1):

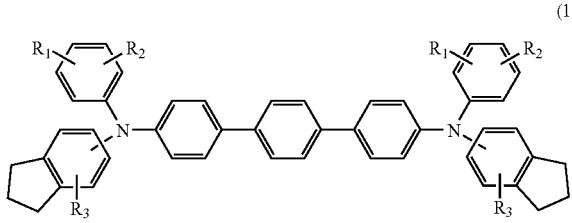

(1)

wherein R1, R2 and R3, which may be the same or different, represent a hydrogen atom, an alkyl group, an alkoxy group, an aralkyl group, a halogen atom, a disubstituted amino group or a substituted or unsubstituted phenyl group, and R1 and R2 may form a ring in combination;

an electrophotographic photoconductor comprising one or more p-terphenyl compounds represented by the following general formula (2):

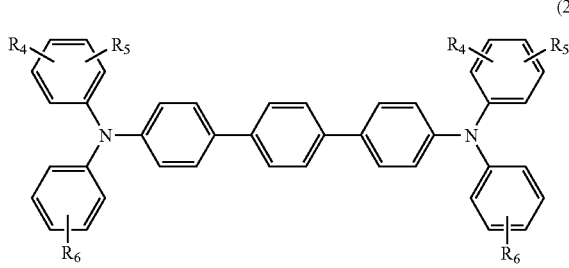

(2)

wherein R4 and R5, which are different from each other, represent an alkyl group, an alkoxy group, an aralkyl group, a halogen atom, a disubstituted amino group or a substituted or unsubstituted phenyl group, and R6 represents a hydrogen atom, an alkyl group, an alkoxy group, an aralkyl group, a halogen atom, a disubstituted amino group or a substituted or unsubstituted phenyl group; and further, an electrophotographic photoconductor comprising one or more p-terphenyl compounds represented by the above-mentioned general formula (1) or general formula (2), and one or more p-terphenyl compounds represented by the following general formula (3):

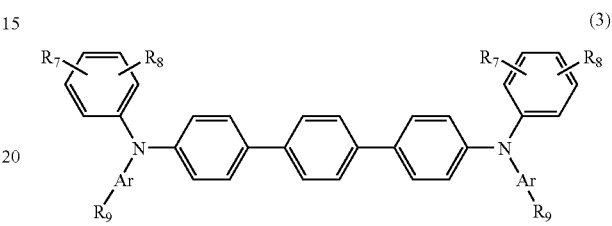

(3)

wherein R7 and R8, which may be the same or different, represent a hydrogen atom, an alkyl group, an alkoxy group, an aralkyl group, a halogen atom, a disubstituted amino group or a substituted or unsubstituted phenyl group, Ar represents a bivalent group of a substituted or unsubstituted aromatic hydrocarbon (excluding indan), and R9 represents a hydrogen atom, an alkyl group, an alkoxy group, an aralkyl group, a halogen atom, a disubstituted amino group or a substituted or unsubstituted phenyl group, wherein when Ar is an unsubstituted phenyl group and either one of R7 and R8 is a hydrogen atom, then the other is a substituent group different from R9 or is the same substituent group having a different substituted position, provided that when either one of R7 and R8 is an alkoxy group, the case where the other and R9 are hydrogen atoms at the same time is excluded.

According to the invention, a p-terphenyl compound has improved solubility in an organic solvent, and there can be provided an electrophotographic photoconductor excellent in drift mobility, satisfying photoconductor characteristics and having high sensitivity and high durability.

Figure 1:
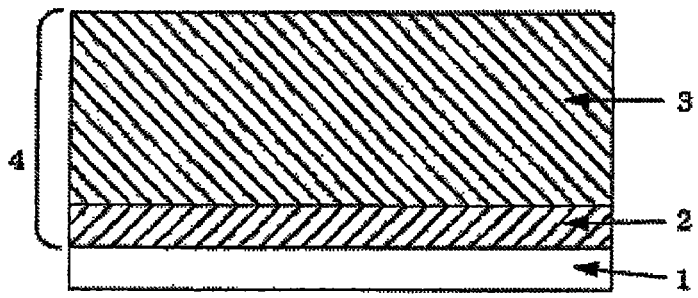
FIG. 1 is a schematic cross sectional view showing a layer structure of a functionally separated type electrophotographic photoconductor.

The reference numerals in the drawings denote the followings:

1: Electroconductive Support
2: Charge Generating Layer
3: Charge Transporting Layer
4: Photosensitive Layer
5: Undercoat Layer
6: Charge Transporting Material-Containing Layer
7: Charge Generating Material
8: Protective Layer

BEST MODE FOR CARRYING OUT THE INVENTION

Specific examples of the p-terphenyl compounds represented by the above-mentioned general formula (1) or general formula (2) include the following compounds, which may be a mixture of isomers different in the substituted position, but are not limited to these compounds in the invention.

Compound No. 1

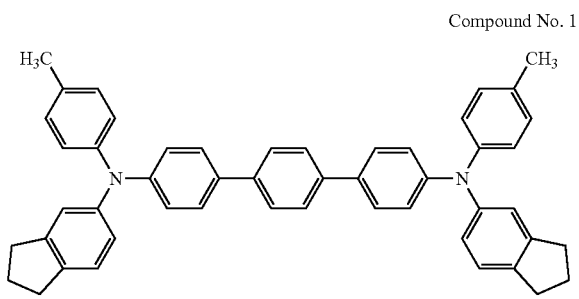

Compound No. 2

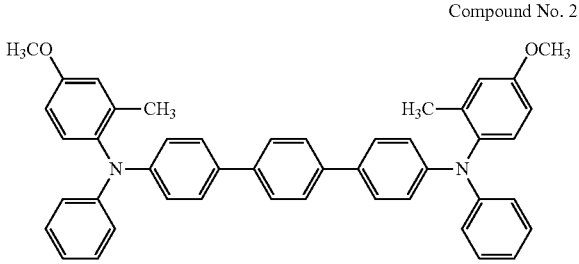

Compound No. 3

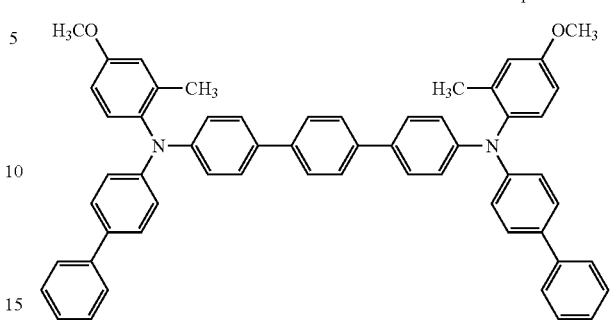

Compound No. 4

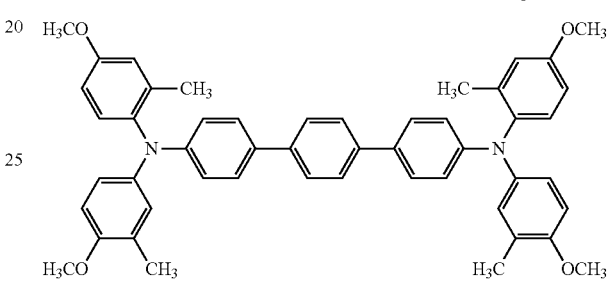

Compound No. 5

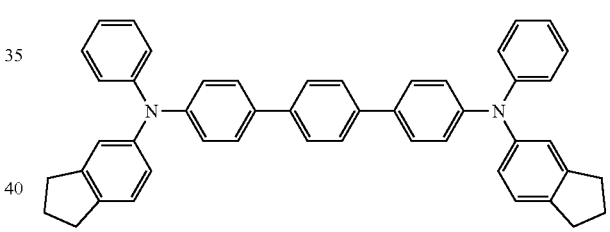

Compound No. 6

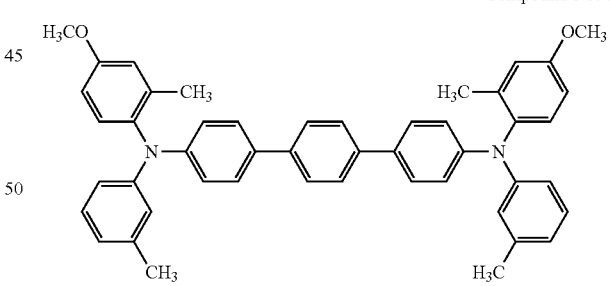

Compound No. 7

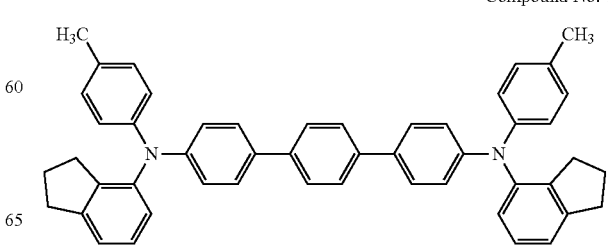

Compound No. 8
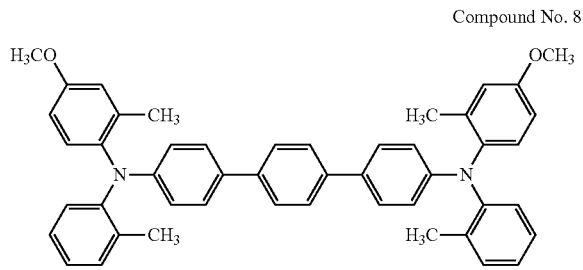

Compound No. 13
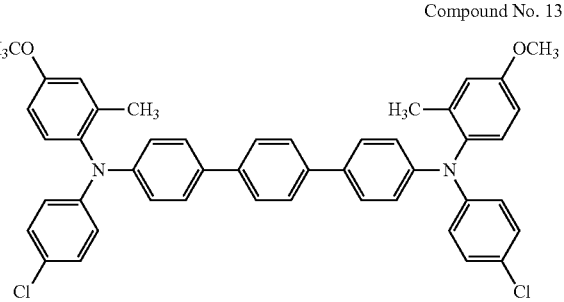

Compound No. 9
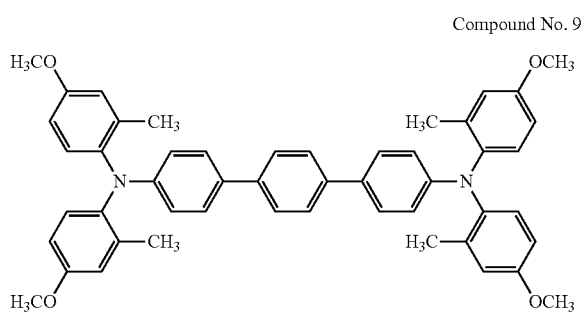

Compound No. 14
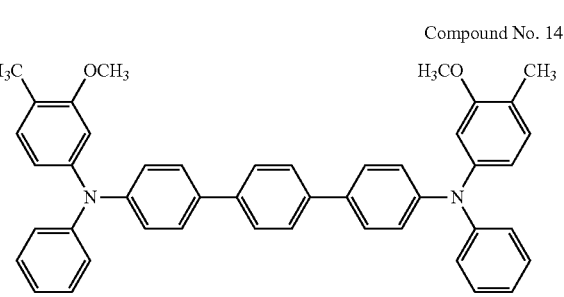

Compound No. 10
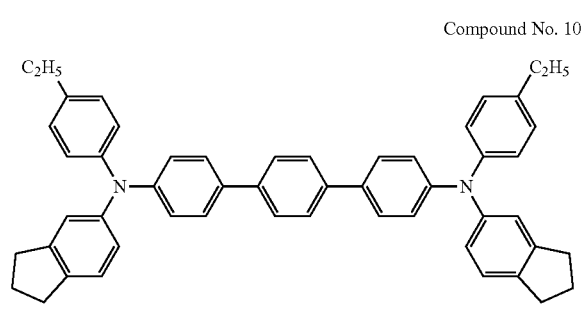

Compound No. 15
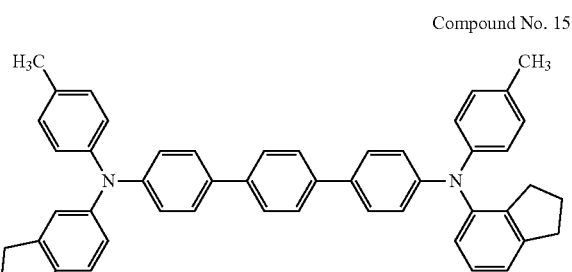

Compound No. 11
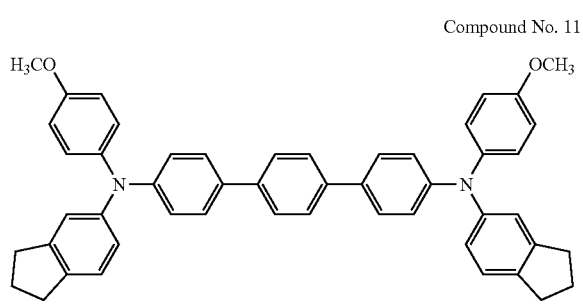

Compound No. 16
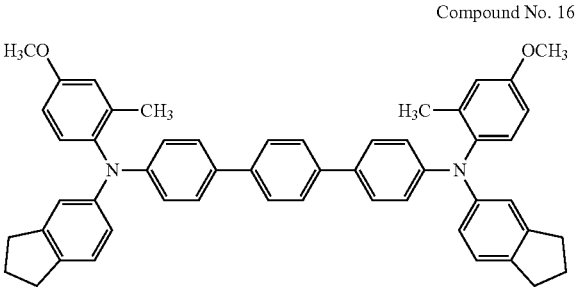

Compound No. 12
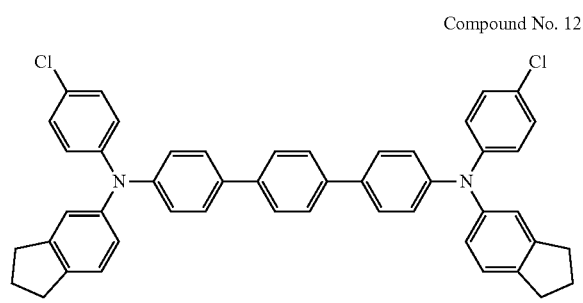

The electrophotographic photoconductor of the invention has a photosensitive layer comprising one or more p-terphenyl compounds represented by the above-mentioned general formula (1) or general formula (2), or has a photosensitive layer comprising one or more p-terphenyl compounds represented by the above-mentioned general formula (1) or general formula (2) and one or more p-terphenyl compounds represented by the above-mentioned general formula (3).

Specific examples of the p-terphenyl compounds represented by the above-mentioned general formula (3) include the following compounds, which may be a mixture of isomers different in the substituted position, but are not limited to these compounds in the invention.

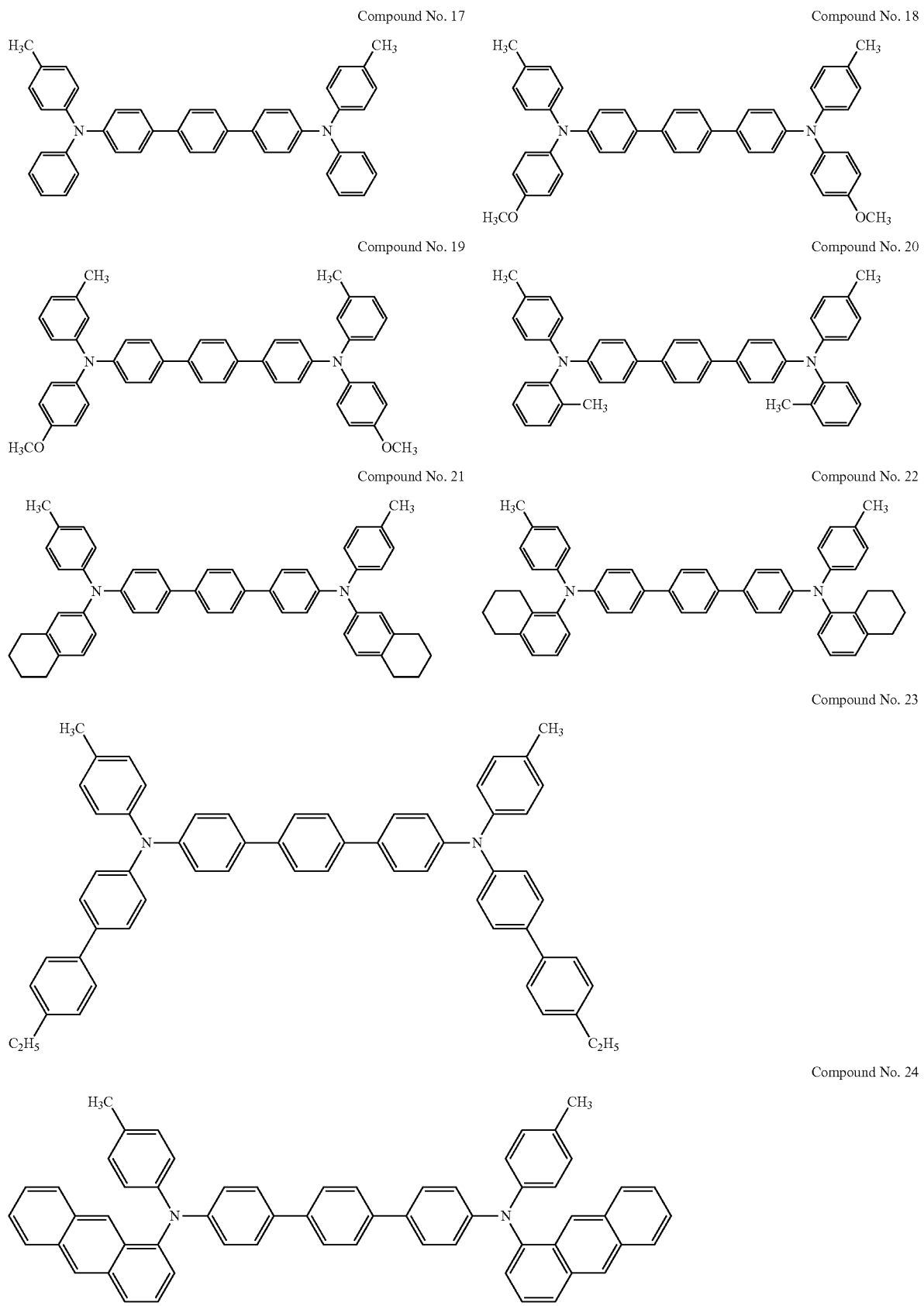

-continued

Compound No. 25

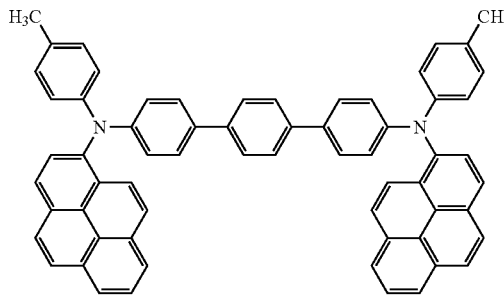

Compound No. 26

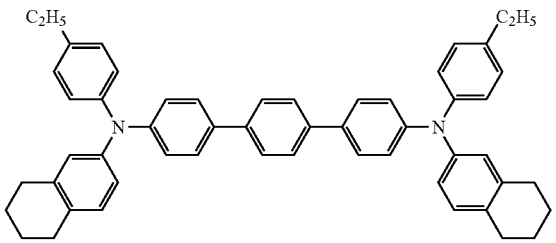

As the form of a photosensitive layer, various forms are present. and the photosensitive layer of the electrophotographic photoconductor of the invention may be any of them. Typical examples of these photoconductors are shown in FIGS. 1 to 7.

Figure 2:
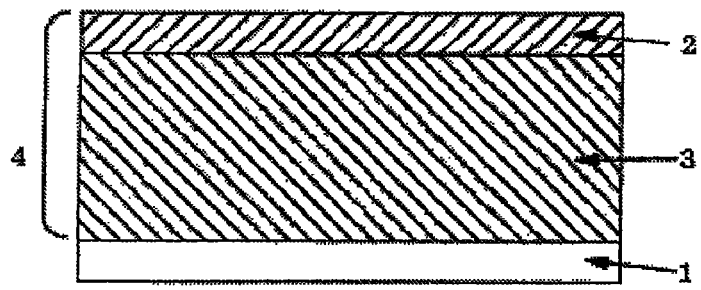
FIG. 2 is a schematic cross sectional view showing another layer structure of a functionally separated type electrophotographic photoconductor.
Figure 3:
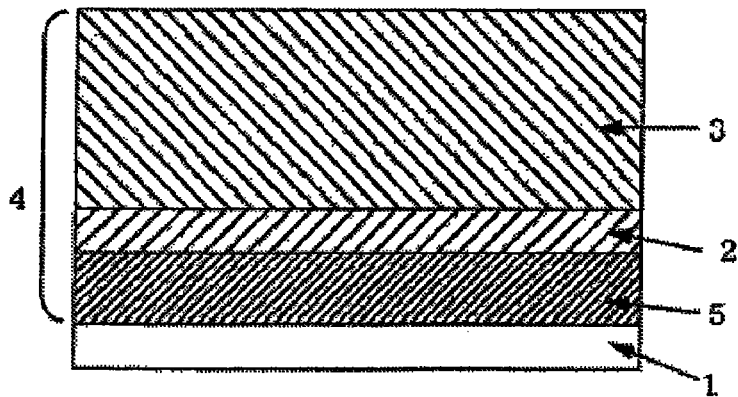
FIG. 3 is a schematic cross sectional view showing a layer structure of a functionally separated type electrophotographic photoconductor in which an undercoat layer is provided between a charge generating layer and an electroconductive support.
Figure 4:
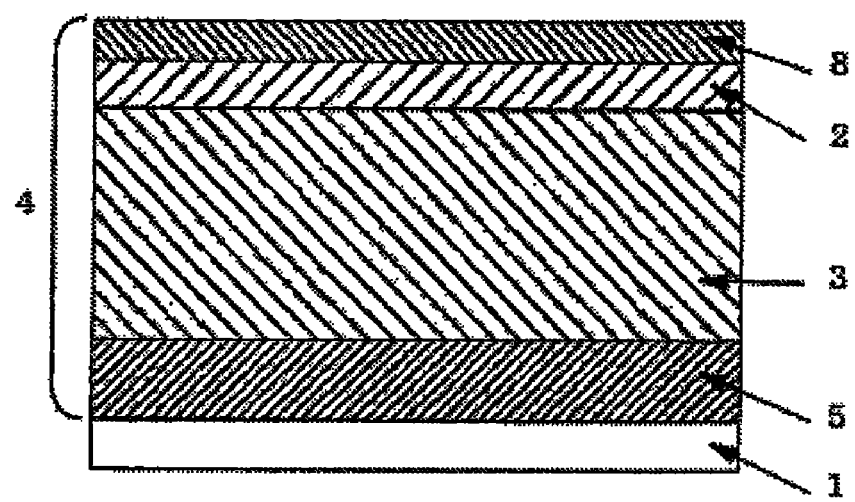
FIG. 4 is a schematic cross sectional view showing a layer structure of a functionally separated type electrophotographic photoconductor in which an undercoat layer is provided between a charge transporting layer and an electroconductive support and a protective layer is provided on a charge generating layer.
Figure 5:
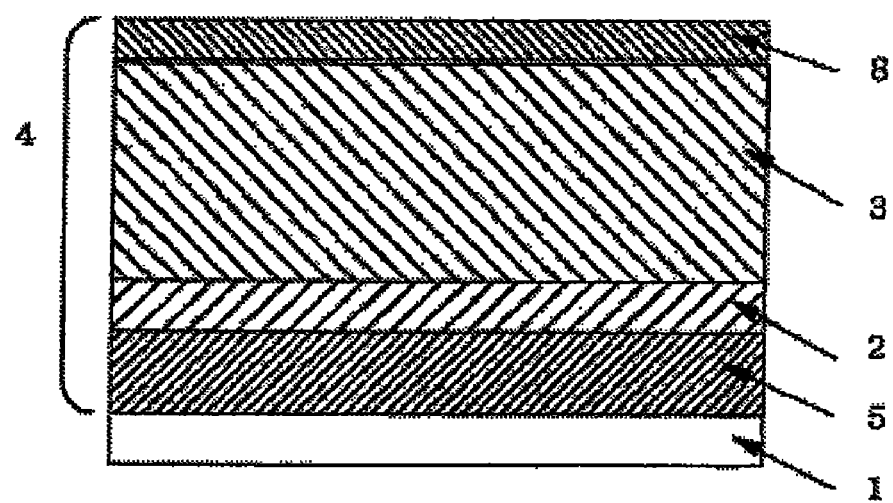
FIG. 5 is a schematic cross sectional view showing a layer structure of a functionally separated type electrophotographic photoconductor in which an undercoat layer is provided between a charge generating layer and an electroconductive support and a protective layer is provided on a charge transporting layer.
Figure 6:
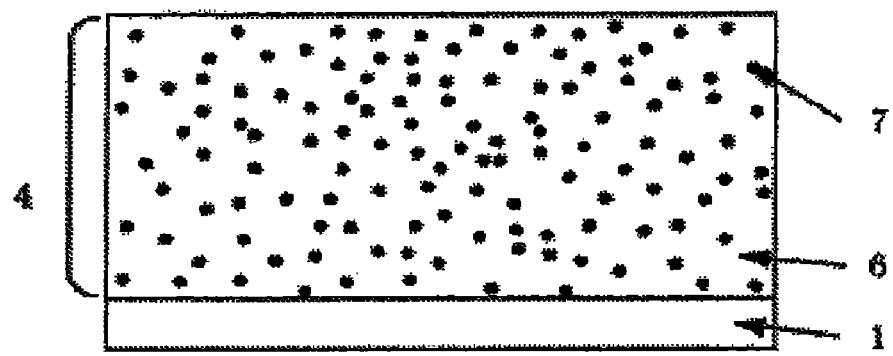
FIG. 6 is a schematic cross sectional view showing a layer structure of a monolayer type electrophotographic photoconductor.
Figure 7:
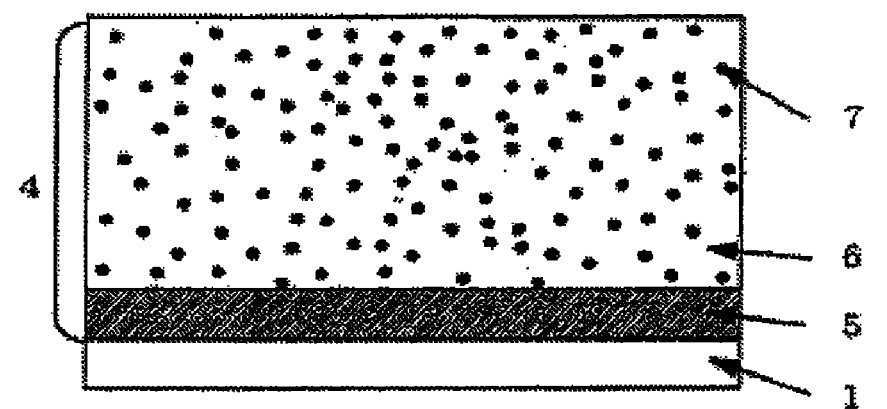
FIG. 7 is a schematic cross sectional view showing a layer structure of a monolayer type electrophotographic photoconductor in which an undercoat layer is provided between a photosensitive layer and an electroconductive support.

In FIGS. 1 and 2, there is provided on an electroconductive support 1 a photosensitive layer 4 comprising a laminate of a charge generating layer 2 containing a charge generating material as a main component and a charge transporting layer 3 containing a charge transporting material and a binder resin as main components. At this time, as shown in FIGS. 3, 4 and 5, the photosensitive layer 4 may be provided with the interposition of an undercoat layer 5 provided on the electroconductive support 1 for adjusting charge, and a protective layer 8 may be provided as an outermost layer. Further, in the invention, as shown in FIGS. 6 and 7, a photosensitive layer 4 comprising a charge generating material 7 dissolved or dispersed in a layer 6 containing the charge transporting material and the binder resin as main components may be provided on the electroconductive support 1 directly or with the interposition of the undercoat layer 5.

The electrophotographic photoconductor of the invention as exemplified above can be prepared according to conventional methods. For example, a coating solution is prepared by dissolving the above-mentioned p-terphenyl compound represented by general formula (1), (2) or (3), together with the binder resin, in a solvent, and adding the charge generating material and optionally a sensitizing dye, an electron transporting compound, an electron attractive compound, a plasticizer, a pigment or other additives, and is applied onto the electroconductive support and dried to form a photosensitive layer having a thickness of several micron meters to several tens micron meters, thereby producing the electrophotographic photoconductor. When the photosensitive layer comprises two layers of the charge generating layer and the charge transporting layer, it can be prepared by laminating the charge transporting layer on the charge generating layer, or forming the charge generating layer on the charge transporting layer. Further, the photoconductor thus produced may be provided with an undercoat layer, an adhesive layer, an intermediate layer or a protective layer as needed.

The solvents for the preparation of the coating solutions include polar organic solvents such as tetrahydrofuran, 1,4-dioxane, methyl ethyl ketone, cyclohexanone, acetonitrile, N,N-dimethylformamide and ethyl acetate, aromatic organic solvents such as toluene and xylene, chlorine-based hydrocarbon solvents such as dichloromethane and dichloroethane, and the like. The solvents having high solubility to the above-mentioned p-terphenyl compounds represented by general formulas (1) to (3) and binder resins are suitably used.

The sensitizing dyes include, for example, triaryl-methane dyes such as methyl violet, brilliant green, crystal violet and acid violet, xanthene dyes such as rhodamine B, eosin S and rose Bengal, thiazine dyes such as methylene blue, pyrylium dyes such as a benzopyrylium salt, thiapyrylium dyes, cyanine dyes and the like.

Further, the electron attractive compounds which form electron transporting complexes with the p-terphenyl compounds include, for example, quinones such as chloranil, 2,3-dichloro-1,4-naphthoquinone, aldehydes such as 4-nitrobenzaldehyde, ketones such as 9-benzoylanthracene, indanedione, 3,5-dinitrobenzophenone, 2,4,7-trinitrofluorenone and 2,4,5,7-tetranitrofluorenone, acid anhydrides such as phthalic anhydride and 4-chloronaphthalic anhydride, cyano compounds such as tetracyanoethylene, terephthalalmalenonitrile, and 9-anthrylmethylidenemalenonitrile and phthalides such as 3-benzalphthalide and 3-($\alpha$-cyano-p-nitrobenzal)-4,5,6,7-tetrachlorophthalide.

The binder resins include polymers and copolymers of vinyl compounds such as styrene, vinyl acetate, vinyl chloride, an acrylic ester, a methacrylic ester and butadiene, and various resins having compatibility with the p-terphenyl compounds, such as a polyvinyl acetal, a polycarbonate, a polyester, a polyphenylene oxide, a polyurethane, a cellulose ester, a phenoxy resin, a silicone resin and an epoxy resin. The amount of the binder resin used is usually from a 0.4-fold to a 10-fold excess by weight, and preferably form a 0.5-fold to a 5-fold excess by weight, in relation to the p-terphenyl compound.

Further, the photosensitive layer of the invention may contain a well-known plasticizer in order to improve film forming properties, flexibility and mechanical strength. The plasticizers include, for example, a phthalic acid ester, a phosphoric acid ester, a chlorinated paraffin, methyl naphthalene, an epoxy compound, a chlorinated aliphatic acid ester and the like.

Furthermore, as the electroconductive support on which the photosensitive layer is formed, there is usable a material used in a well-known electrophotographic photoconductor. Examples thereof include a drum or sheet of a metal such as aluminum, stainless steel or copper, a laminate of such a metal, a vapor-deposited material, a plastic film, plastic drum, paper or paper tube coated with a metal powder, carbon black, copper iodide or an electroconductive material of a high molecular electrolyte together with an appropriate binder to perform electroconductive treatment, a plastic film or plastic

EXAMPLES

Embodiments of the invention will be illustrated in greater detail with reference to the following examples, but the invention should not be construed as being limited to these examples. "Parts" in the examples are given by weight.

Example 1

Synthesis Example 1

Synthesis of Compound No. 1

After 33.3 g (0.25 mol) of 5-aminoindane (manufactured by Tokyo Chemical Industry Co., Ltd.) was dissolved in 250 ml of glacial acetic acid, the solution was heated at 50° C., and 51.0 g (0.5 mol) of acetic anhydride was added dropwise. After the termination of the dropping, stirring was performed for 4 hours. After the termination of the reaction, the reaction solution was poured into 1500 ml of ice water with stirring. Precipitated crystals were separated by filtration, and washed with 1000 ml of water. The resulting crystals were dried to obtain 37.06 g of 5-(N-acetylamino)indane (yield: 84.6%, melting point: 100.5 to 103.5° C.).

5-(N-Acetylamino)indane (26.28 g (0.15 mol)), 43.61 g (0.20 mol) of iodotoluene, 25.88 g (0.188 mol) of anhydrous potassium carbonate and 2.38 g (0.038 mol) of copper powder were mixed, and heated up to 200° C. while introducing nitrogen gas, followed by stirring for 6 hours. After the termination of the reaction, cooling was conducted, and 22.3 g of potassium hydroxide dissolved in 20 ml of water and 50 ml of isoamyl alcohol were added to perform hydrolysis at 130° C. for 2 hours. After the termination of the hydrolysis, 250 ml of water was added, and isoamyl alcohol was removed by azeotropic distillation. Then, 200 ml of toluene was added to dissolve the reaction product. After filtration, dehydration was performed with magnesium sulfate. After magnesium sulfate was removed by filtration, the filtrate was concentrated, and purified by column chromatography (carrier: silica gel, eluent: toluene:hexane 1:4) to obtain 32.3 g of indane-5-yl-p-tolylamine.

Indane-5-yl-p-tolylamine (18.1 g (0.081 mol)), 18.9 g (0.039 mol) of 4,4"-diiodo-p-terphenyl, 7.2 g (0.052 mol) of anhydrous potassium carbonate, 0.76 g (0.012 mol) of copper powder and 30 ml of n-dodecane were mixed, and heated up to 200 to 210° C. while introducing nitrogen gas, followed by stirring for 30 hours. After the termination of the reaction, the reaction product was extracted with 400 ml of toluene, and insoluble matter was removed by filtration. Then, the filtrate was concentrated to dryness. The resulting solid matter was purified by column chromatography (carrier: silica gel, eluent: toluene:hexane=1:4) to obtain 19.9 g of N,N'-bisindane-5-yl-N,N'-di-p-tolyl-4,4"-diamino-p-terphenyl (compound No. 1) (yield: 75.7%, melting point: 207.4 to 208.1° C.).

Figure 8:
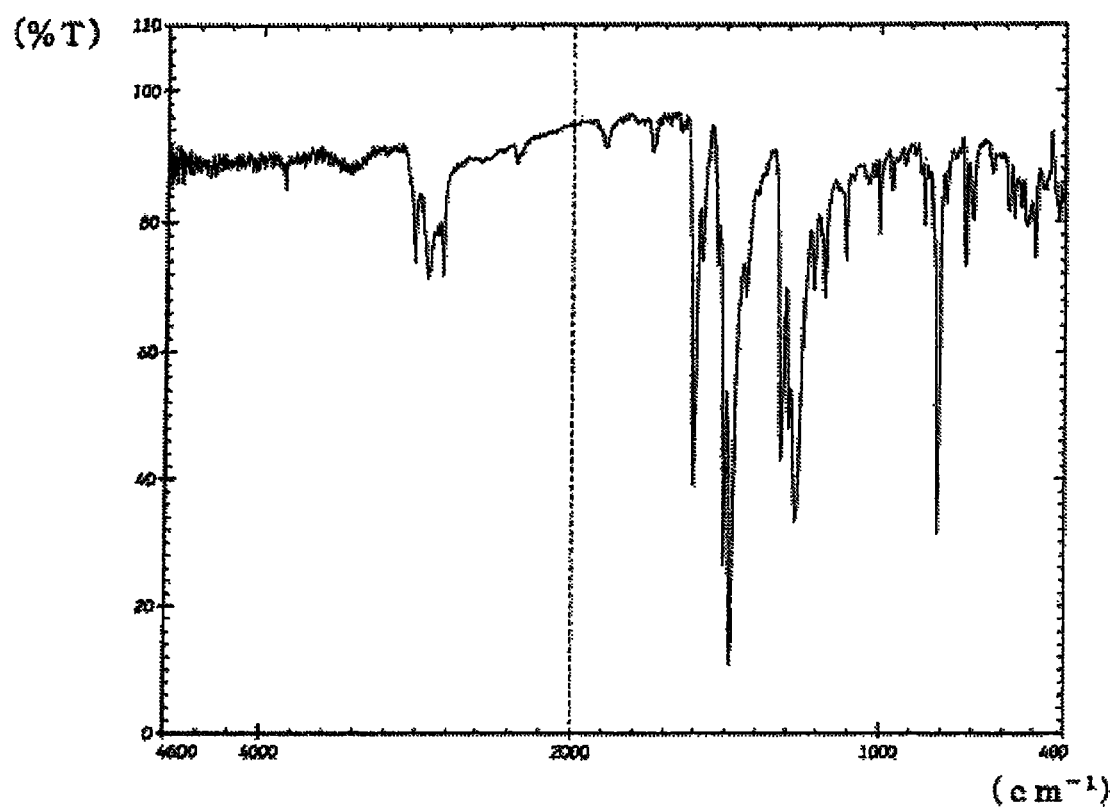
FIG. 8 is an IR spectrum of compound No. 1 (Synthesis Example 1).

This was identified as compound No. 1 by elemental analysis and IR measurement. An IR spectrum is shown in FIG. 8. The elemental analysis values are as follows: carbon: 89.13% (89.25%), hydrogen: 6.63% (6.59%), nitrogen: 4.24% (4.16%) (calculated values are shown in parentheses).

Example 2

Synthesis Example 2

Synthesis of Compound No. 2

(4-Methoxy-2-methylphenyl)phenylamine (14.1 g (0.066 mol)), 14.5 g (0.030 mol) of 4,4"-diiodo-p-terphenyl, 5.0 g (0.036 mol) of anhydrous potassium carbonate, 0.38 g (0.006 mol) of copper powder and 15 ml of n-dodecane were mixed, and heated up to 200 to 210° C. while introducing nitrogen gas, followed by stirring for 30 hours. After the termination of the reaction, the reaction product was extracted with 400 ml of toluene, and insoluble matter was removed by filtration. Then, the filtrate was concentrated to dryness. The resulting solid matter was purified by column chromatography (carrier: silica gel, eluent: toluene:hexane=1:2) to obtain 15.7 g of N,N'-di(4-methoxy-2-methylphenyl)-N,N'-diphenyl-4,4"-diamino-p-terphenyl (compound No. 2) (yield: 80.0%, melting point: 180.8 to 183.4° C.).

Figure 9:
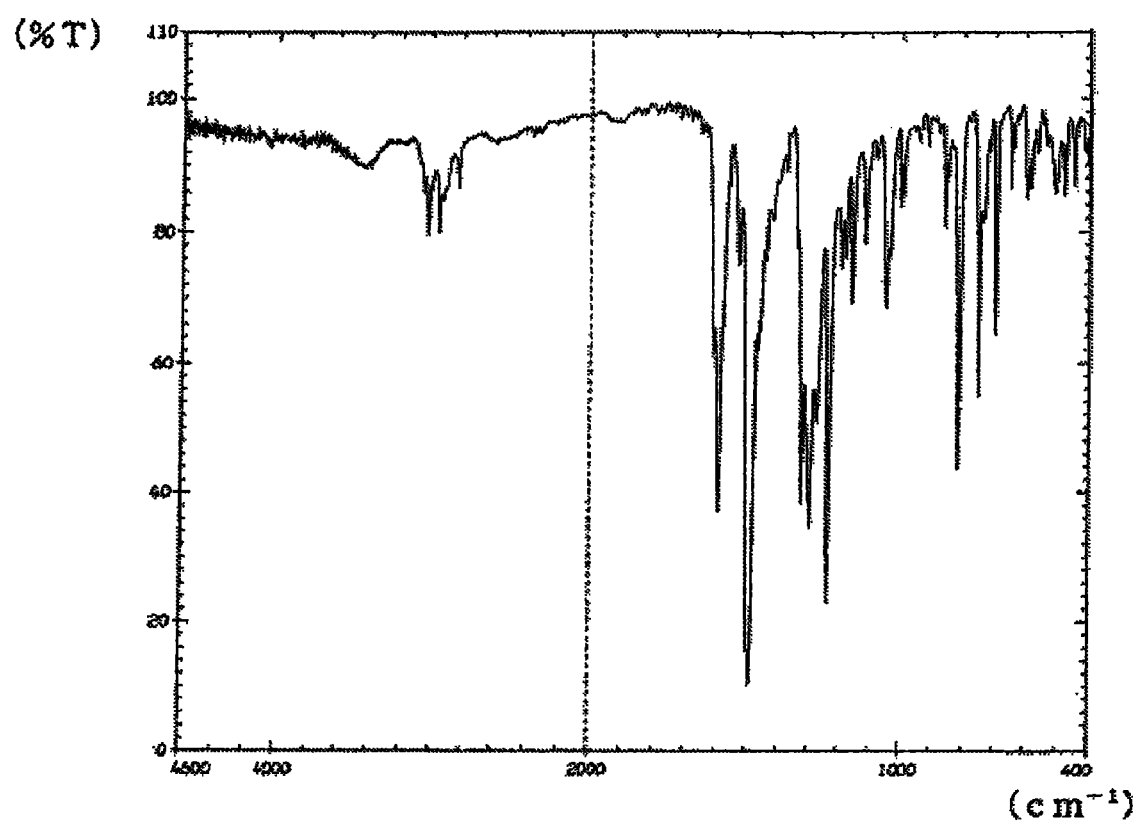
FIG. 9 is an IR spectrum of compound No. 2 (Synthesis Example 2).

This was identified as compound No. 2 by elemental analysis and IR measurement. An IR spectrum is shown in FIG. 9. The elemental analysis values are as follows: carbon: 84.67% (84.63%), hydrogen: 6.23% (6.18%), nitrogen: 4.26% (4.29%) (calculated values are shown in parentheses).

Example 3

Synthesis Example 3

Synthesis of Compound No. 3

After 23.3 g (0.17 mol) of 4-methoxy-2-methylaniline (manufactured by Tokyo Chemical Industry Co., Ltd.) was dissolved in 20 ml of glacial acetic acid, the solution was heated at 50° C., and 51.0 g (0.5 mol) of acetic anhydride was added dropwise. After the termination of the dropping, stirring was performed for 3 hours. After the termination of the reaction, the reaction solution was poured into 500 ml of ice water, followed by stirring. Precipitated crystals were separated by filtration, and washed with 400 ml of water. The resulting crystals were dried to obtain 23.77 g of 4-methoxy-2-methylacetanilide (yield: 78.0%).

4-Methoxy-2-methylacetanilide (20.61 g (0.115 mol)), 24.11 g (0.050 mol) of 4,4"-diiodo-p-terphenyl, 17.97 g (0.130 mol) of anhydrous potassium carbonate, 1.27 g (0.020 mol) of copper powder and 25 ml of n-dodecane were mixed, and heated up to 205° C. while introducing nitrogen gas, followed by stirring for 5 hours. After the termination of the reaction, cooling was conducted, and 9.8 g of potassium hydroxide dissolved in 5 ml of water and 75 ml of isoamyl alcohol were added to perform hydrolysis at 120° C. for 4 hours. After the termination of the hydrolysis, 180 ml of water was added, and isoamyl alcohol was removed by azeotropic distillation, followed by filtration. Crystals separated by the filtration were washed with 100 ml of water and further with 100 ml of methanol, and dried to obtain 20.84 g of 4,4"-bis(4-methoxy-2-methylphenylamino)-p-terphenyl (yield: 83.3%).

4,4"-Bis(4-methoxy-2-methylphenylamino)-p-terphenyl (9.00 g (0.018 mol)), 1.1 g (0.040 mol) of 4-iodobiphenyl, 14.4 g (0.104 mol) of anhydrous potassium carbonate, 1.02 g (0.016 mol) of copper powder and 30 ml of n-dodecane were mixed, and heated up to 200 to 220° C. while introducing nitrogen gas, followed by stirring for 3 hours. After the termination of the reaction, the reaction product was extracted with 400 ml of toluene, and insoluble matter was removed by filtration. Then, the filtrate was concentrated to dryness. The resulting solid matter was purified by column chromatography (carrier: silica gel, eluent: toluene:hexane=2:1) to obtain 9.66 g of N,N'-bis-biphenyl-4-yl-N,N'-di-4-methoxy-2-methylphenyl-4,4"-diamino-p-terphenyl (compound No. 3) (yield: 66.7%, melting point: 232.6 to 233.2° C.).

Figure 10:
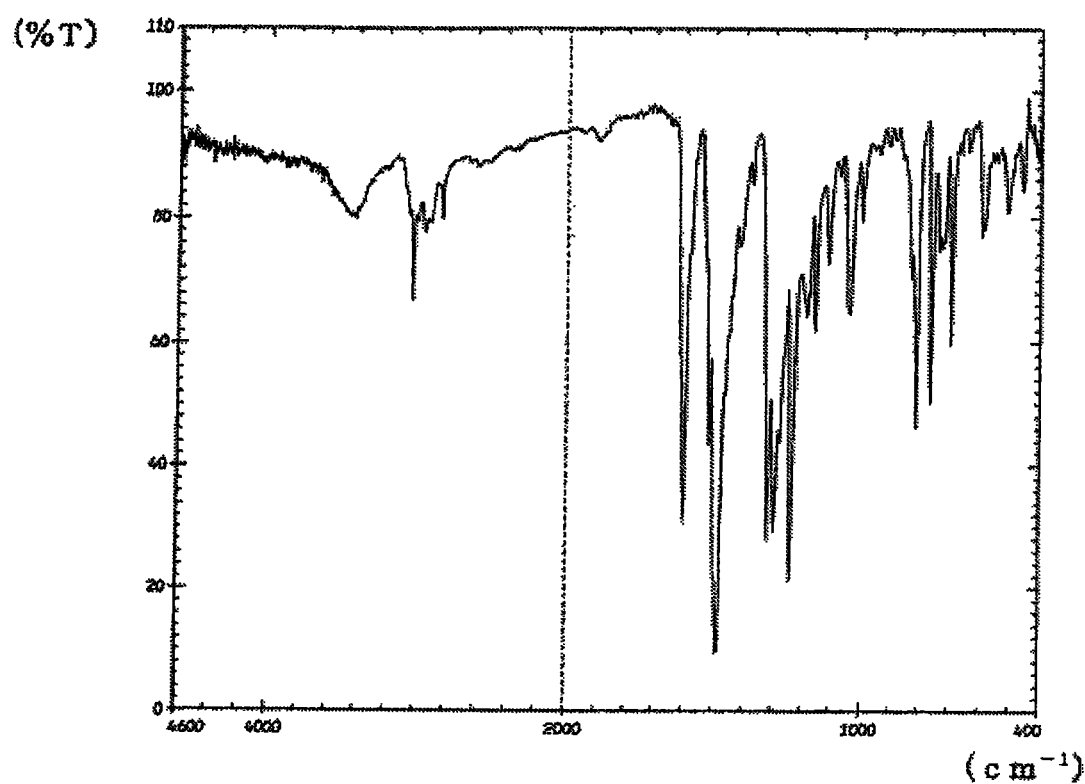
FIG. 10 is an IR spectrum of compound No. 3 (Synthesis Example 3).

This was identified as compound No. 3 by elemental analysis and IR measurement. An IR spectrum is shown in FIG. 10. The elemental analysis values are as follows: carbon: 86.50% (86.54%), hydrogen: 6.09% (6.01%), nitrogen: 3.53% (3.48%) (calculated values are shown in parentheses).

Example 4

Synthesis Example 4

Synthesis of Compound No. 17

Phenyl-p-tolylamine (11.5 g (0.063 mol)), 14.5 g (0.030 mol) of 4,4"-diiodo-p-terphenyl, 5.0 g (0.036 mol) of anhydrous potassium carbonate, 0.38 g (0.006 mol) of copper powder and 15 ml of n-dodecane were mixed, and heated up to 200 to 210° C. while introducing nitrogen gas, followed by stirring for 30 hours. After the termination of the reaction, the reaction product was extracted with 400 ml of toluene, and insoluble matter was removed by filtration. Then, the filtrate was concentrated to dryness. The resulting solid matter was purified by column chromatography (carrier: silica gel, eluent: toluene:hexane=1:4) to obtain 13.6 g of N,N'-diphenyl-N,N'-di-p-tolyl-4,4"-diamino-p-terphenyl (compound No. 17) (yield: 76.4%, melting point: 167.2 to 168.2° C.).

Figure 11:
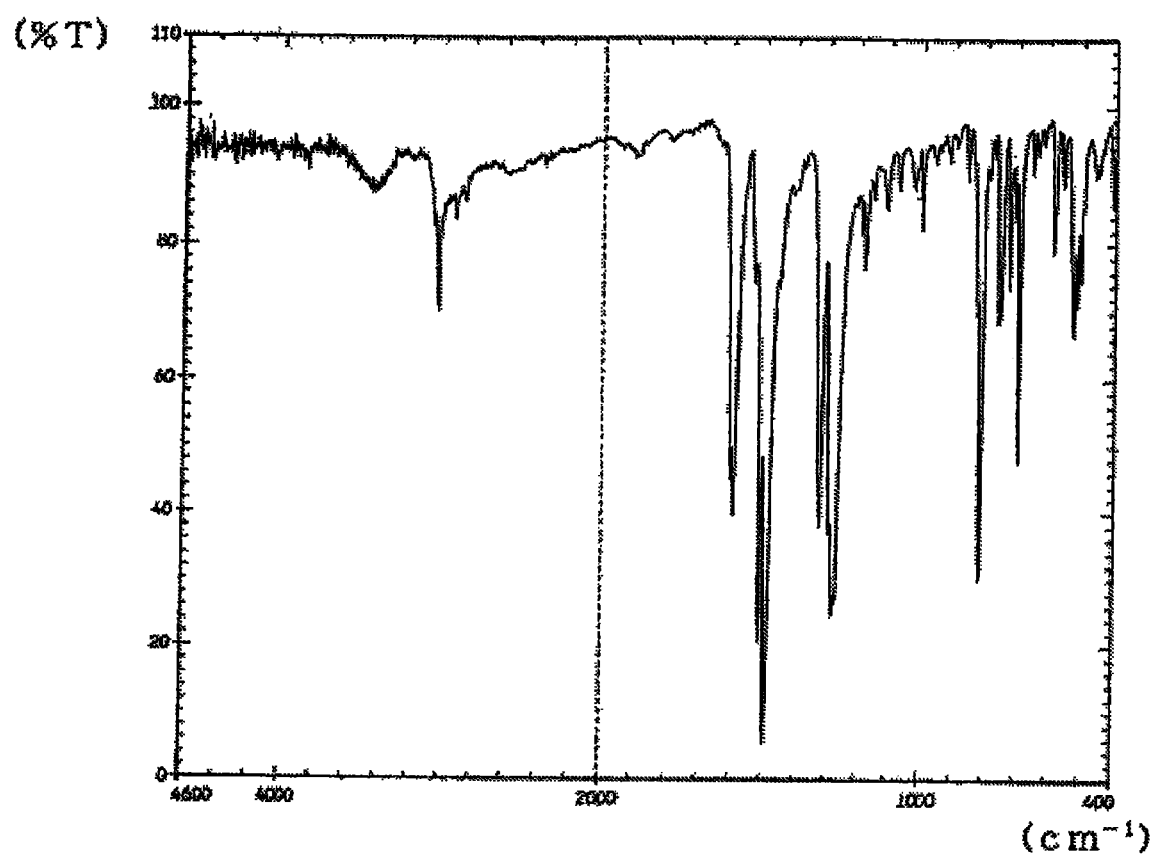
FIG. 11 is an IR spectrum of compound No. 17 (Synthesis Example 4).

This was identified as compound No. 17 by elemental analysis and IR measurement. An IR spectrum is shown in FIG. 11. The elemental analysis values are as follows: carbon: 89.23% (89.15%), hydrogen: 6.14% (6.12%), nitrogen: 4.60% (4.73%) (calculated values are shown in parentheses).

Synthesis Comparative Example 1

Synthesis of Comparative Compound No. 1

As a comparative compound, the following compound (comparative compound No. 1) was synthesized.

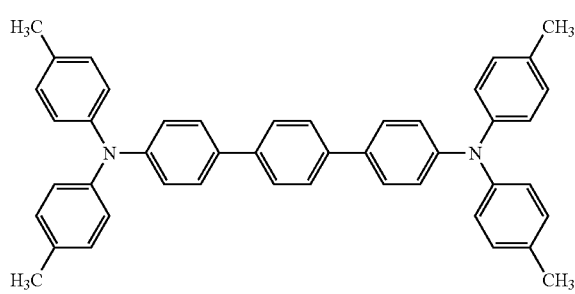

Di-p-tolylamine (12.8 g (0.065 mol)), 14.0 g (0.029 mol) of 4,4"-diiodo-p-terphenyl, 4.7 g (0.034 mol) of anhydrous potassium carbonate, 0.51 g (0.008 mol) of copper powder and 30 ml of n-dodecane were mixed, and heated up to 200 to 210° C. while introducing nitrogen gas, followed by stirring for 30 hours. After the termination of the reaction, the reaction product was extracted with 500 ml of toluene, and insoluble matter was removed by filtration. Then, the filtrate was concentrated to dryness. The resulting solid matter was purified by column chromatography (carrier: silica gel, eluent: toluene:hexane=1:2) to obtain 11.8 g of N,N,N',N'-tetra-p-tolyl-4,4"-diamino-p-terphenyl (comparative compound No. 1) (yield: 65.7%, melting point: 232.5 to 233.5° C.).

Figure 12:
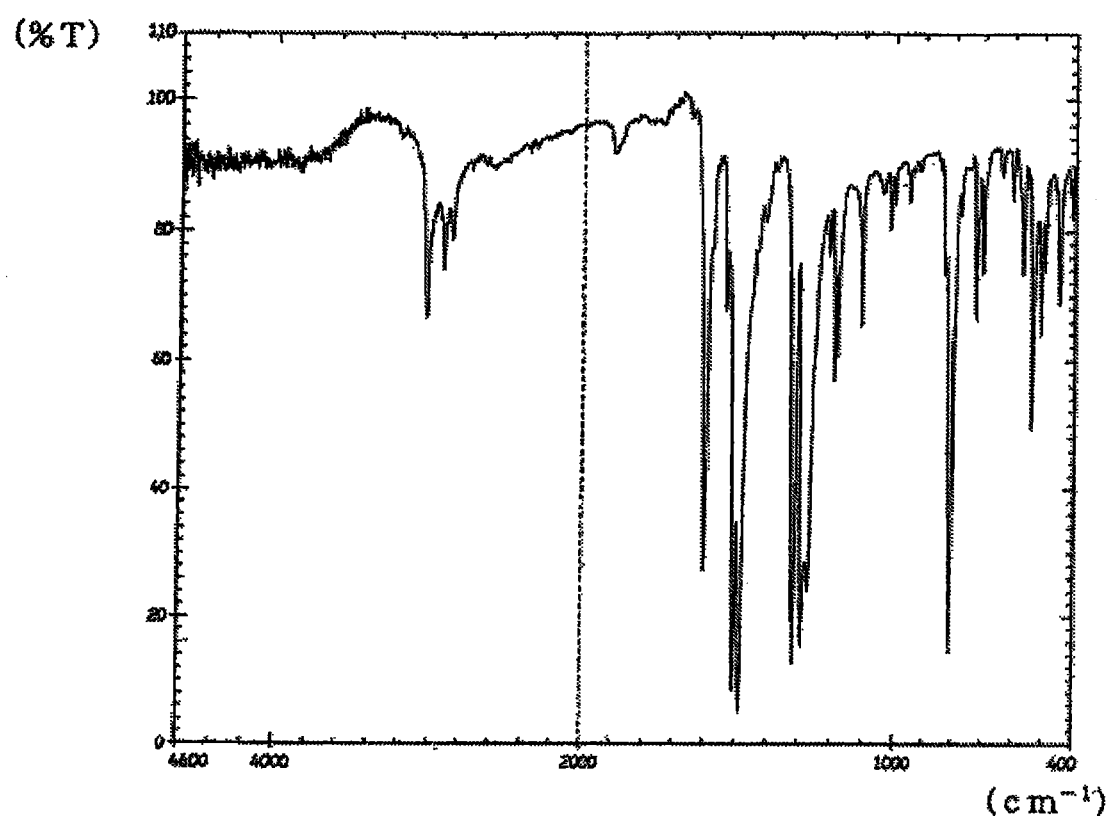
FIG. 12 is an IR spectrum of comparative compound No. 1 (Synthesis Comparative Example 1).

This was identified as comparative compound No. 1 by elemental analysis and IR measurement. An IR spectrum is shown in FIG. 12. The elemental analysis values are as follows: carbon: 89.13% (88.99%), hydrogen: 6.33% (6.49%), nitrogen: 4.54% (4.51%) (calculated values are shown in parentheses).

Example 5

Solubility in Organic Solvents

The solubility of Synthesis Examples 1 to 3 and Synthesis Comparative Example 1 in organic solvents (1,2-dichloroethane, toluene and tetrahydrofuran) at 25° C. was measured. The results are shown in Table 1. The solubility was indicated by the amount of solute (g) based on 100 ml of solvent.

TABLE 1

| Example and Comparative Example | Compound No. | 1,2-Dichloro-ethane | Toluene | Tetrahydro-furan |
|---|---|---|---|---|
| Synthesis Example 1 | 1 | 4.2 | 11.0 | 20.8 |
| Synthesis Example 2 | 2 | 3.5 | 9.3 | 18.1 |
| Synthesis Example 3 | 3 | 30.0 or more | 30.0 or more | 30.0 or more |
| Synthesis Comparative Example 1 | Comparative Compound 1 | 2.3 | 2.2 | 12.4 |

The p-terphenyl compounds of the invention have extremely high solubility in the organic solvents, and coating solutions in which the p-terphenyl compounds are dissolved together with binder resins are excellent in dissolving stability.

Example 6

Photoconductor Example 1

One part of an alcohol-soluble polyamide (Amilan CM-4000, manufactured by Toray Industries, Inc.) was dissolved in 13 parts of methanol, and 5 parts of titanium oxide (Tipaque CR-EL, manufactured by Ishihara Sangyo Kaisha, Ltd.) was added thereto. The mixture was dispersed by a paint shaker for 8 hours to prepare a coating solution for an undercoat layer. Then, the coating solution was applied onto an aluminum surface of an aluminum vapor-deposited PET film with a wire bar and dried at 60° C. for 1 hour to form an undercoat layer having a thickness of 1 μm.

As a charge generating agent, 1.5 parts of titanyl phthalocyanine (charge generating agent No. 1) having strong peaks at diffraction angles (2θ±0.2°) of 9.6, 24.1 and 27.2 in an X-ray diffraction spectrum of Cu—Kα

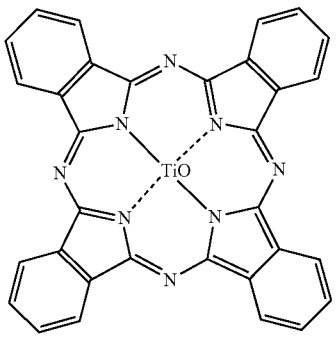

was added to 50 parts of a 3% cyclohexanone solution of a polyvinyl butyral resin (Eslex BL-S, manufactured by Sekisui Chemical Co., Ltd.), and the mixture was dispersed by an ultrasonic dispersing machine for 1 hour. The resulting dispersion was applied onto the above-mentioned undercoat layer with a wire bar, and then, dried at 110° C. under normal pressure for 1 hour to form a charge generating layer having a film thickness of 0.6 μm.

On the other hand, 1.5 parts of the p-terphenyl compound (compound No. 1) synthesized in Synthesis Example 1 was added as a charge transporting agent to 18.75 parts of a 8.0% dichloroethane solution of a polycarbonate resin (Iupilon Z, manufactured by Mitsubishi Engineering-Plastics Corporation), followed by application of an ultrasonic wave to completely dissolve the p-terphenyl compound. This solution was applied onto the above-mentioned charge generating layer with a wire bar, and dried at 110° C. under normal pressure for 30 minutes to form a charge transporting layer having a film thickness of 20 μm, thus preparing photoconductor No. 1.

Example 7

Photoconductor Examples 2 and 3

Photoconductor Nos. 2 and 3 were each prepared in the same manner as in Photoconductor Example 1 with the exception that the charge transporting agent used in Photoconductor Example 1 was changed to the same amounts of the terphenyl compounds (compound Nos. 2 and 3) synthesized in Synthesis Examples 2 and 3, respectively.

Example 8

Photoconductor Example 4

Photoconductor No. 4 was prepared in the same manner as in Photoconductor Example 1 with the exception that the charge transporting agent used in Photoconductor Example 1 was changed to 0.45 part of compound No. 1 and 0.75 part of compound No. 2.

Example 9

Photoconductor Examples 5 and 6

Photoconductors Nos. 5 and 6 were each prepared in the same manner as in Photoconductor Example 4 with the exception that the charge transporting agent used in Photoconductor Example 4 was changed to the same amount of a combination of compound No. 1 and compound No. 4 and the same amount of a combination of compound No. 2 and compound No. 4, respectively.

Photoconductor Comparative Example 1

Photoconductor No. 7 was prepared in the same manner as in Photoconductor Example 1 with the exception that the charge transporting agent used in Photoconductor Example 1 was changed to the same amount of the p-terphenyl compound (comparative compound No. 1) synthesized in Synthesis Comparative Example 1. However, the compound of Synthesis Comparative Example 1 was insoluble, so that the measurement as the photoconductor was impossible.

Example 10

For the photoconductors of Photoconductor Examples 1 to 6, evaluation of electrophotographic properties was carried out using an electrostatic copying test apparatus (trade name: "EPA-8100A"). First, the photoconductors were subjected to corona discharge of −6.5 kV in a dark place, and the charge potential $V_0$ at that time was measured. Then, the photoconductors were exposed to monocolor light of 780 nm at 1.0 μW/cm$^2$, and the half decay exposure amount E1/2 (μJ/cm$^2$) and the residual potential Vr (−V) after exposure for 5 seconds were determined. The results thereof are shown in Table 2.

TABLE 2

| Example and Comparative Example | Photoreceptor No. | Charge Potential $V_0$ (−V) | Half Decay Exposure Amount E½ (μJ/cm$^2$) | Residual Potential Vr (−V) |
|---|---|---|---|---|
| Photoconductor Example 1 | 1 | 809 | 0.18 | 5 |
| Photoconductor Example 2 | 2 | 795 | 0.21 | 10 |
| Photoconductor Example 3 | 3 | 798 | 0.20 | 8 |
| Photoconductor Example 4 | 4 | 811 | 0.20 | 8 |
| Photoconductor Example 5 | 5 | 803 | 0.20 | 7 |
| Photoconductor Example 6 | 6 | 802 | 0.20 | 7 |
| Photoconductor Comparative Example 1 | 7 | Insoluble, so that measurement was impossible. | | |

Example 11

Photoconductor Example 7

As a charge generating agent, 1.5 parts of titanyl phthalocyanine (charge generating agent No. 2) having strong peaks at diffraction angles (2θ±0.2°) of 7.5, 10.3, 12.6, 22.5, 24.3, 25.4 and 28.6 in an X-ray diffraction spectrum of Cu—Kα was added to 50 parts of a 3% cyclohexanone solution of a polyvinyl butyral resin (Eslex BL-S, manufactured by Sekisui Chemical Co., Ltd.), and the mixture was dispersed by an ultrasonic dispersing machine for 1 hour. The resulting dispersion was applied onto an aluminum surface of an aluminum vapor-deposited PET film with a wire bar, and then, dried at 110° C. under normal pressure for 1 hour to form a charge generating layer having a film thickness of 0.2 μm.

On the other hand, 0.9 part of the p-terphenyl compound (compound No. 1) synthesized in Synthesis Example 1 was added as a charge transporting agent to 11.25 parts of a 8.0% dichloroethane solution of a polycarbonate resin (Iupilon Z, manufactured by Mitsubishi Engineering-Plastics Corporation), followed by application of an ultrasonic wave to completely dissolve the p-terphenyl compound. This solution was applied onto the above-mentioned charge generating layer with a wire bar, and dried at 110° C. under normal pressure for 30 minutes to form a charge transporting layer having a film thickness of 10 μm. Further, a translucent gold electrode was vapor deposited on the charge transporting layer to prepare photoconductor No. 8.

Example 12

Photoconductor Examples 8 and 9

Photoconductor Nos. 9 and 10 were each prepared in the same manner as in Photoconductor Example 7 with the exception that the charge transporting agent used in Photoconductor Example 7 was changed to the same amounts of the terphenyl compounds (compound Nos. 2 and 3) synthesized in Synthesis Examples 2 and 3, respectively.

Photoconductor Comparative Example 2

Photoconductor No. 11 was prepared in the same manner as in Photoconductor Example 7 with the exception that the charge transporting agent used in Photoconductor Example 7 was changed to the same amount of the terphenyl compound (comparative compound No. 1) synthesized in Synthesis Comparative Example 1. However, the photoconductor was insoluble.

Example 13

Drift Mobility

For the photoconductors prepared in Photoconductor Examples 7 to 9, the drift mobility was measured. The measurement was made by a time-of-flight method, and the drift mobility was measured at 2×105 V/cm. The results thereof are shown in Table 3.

TABLE 3

| Example and Comparative Example | Photoconductor No. | Drift Mobility [cm$^2$/V · s] |
| --- | --- | --- |
| Photoconductor Example 7 | 8 | $1.0 \times 10^{-4}$ |
| Photoconductor Example 8 | 9 | $4.4 \times 10^{-5}$ |
| Photoconductor Example 9 | 10 | $5.1 \times 10^{-5}$ |
| Photoconductor Comparative Example 7 | 11 | Insoluble, so that measurement was impossible. |

As described above, the p-terphenyl compound according to the invention is improved in solubility in an organic solvent, and can provide an electrophotographic photoconductor, excellent in drift mobility, satisfying photoconductor characteristics, and having high sensitivity and high durability.

While the invention has been described in detail and with reference to specific embodiments thereof, it will be apparent to one skilled in the art that various changes and modifications can be made therein without departing from the spirit and scope thereof.

The present application is based on Japanese Patent Application No. 2004-154722 filed on May 25, 2004, and the contents thereof are herein incorporated by reference.

INDUSTRIAL APPLICABILITY

The p-terphenyl compound according to the invention is useful as a charge transporting agent which can realize an electrophotographic photoconductor improved in solubility in an organic solvent, satisfying photoconductor characteristics, and having high sensitivity and high durability.

The invention claimed is:

1. A p-terphenyl compound represented by the following general formula (1):

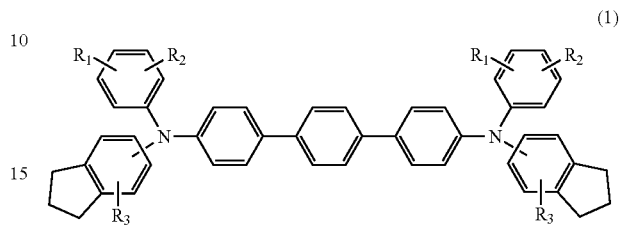

(1)

wherein R1, R2 and R3, which may be the same or different, represent a hydrogen atom, an alkyl group, an alkoxy group, an aralkyl group, a halogen atom, a disubstituted amino group or a substituted or unsubstituted phenyl group, and R1 and R2 may form a ring in combination.

2. An electrophotographic photoconductor comprising one or more p-terphenyl compounds represented by the following general formula (1):

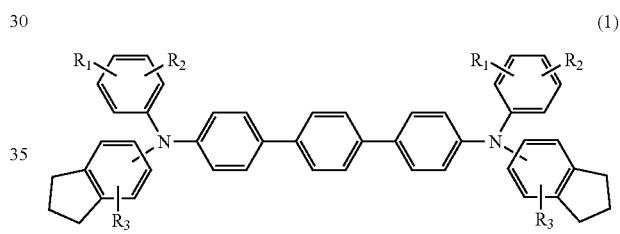

(1)

wherein R1, R2 and R3, which may be the same or different, represent a hydrogen atom, an alkyl group, an alkoxy group, an aralkyl group, a halogen atom, a disubstituted amino group or a substituted or unsubstituted phenyl group, and R1 and R2 may form a ring in combination.

3. The electrophotographic photoconductor according to claim 2, which further comprises one or more p-terphenyl compounds represented by the following general formula (3):

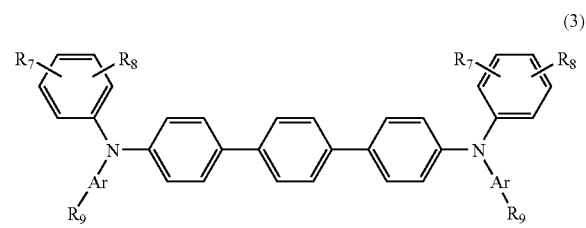

(3)

wherein R7 and R8, which may be the same or different, represent a hydrogen atom, an alkyl group, an alkoxy group, an aralkyl group, a halogen atom, a disubstituted amino group or a substituted or unsubstituted phenyl group, Ar represents a bivalent group of a substituted or unsubstituted aromatic hydrocarbon (excluding indan), and R9 represents a hydrogen atom, an alkyl group, an alkoxy group, an aralkyl group, a halogen atom, a di-substituted amino group or a substituted or unsubstituted phenyl group, wherein when Ar is an unsubstituted phenyl group and either one of R7 and R8 is a hydrogen atom, then the other is a substituent group different from R9 or is the same substituent group having a different substituted position, provided that when either one of R7 and R8 is an alkoxy group, the case where the other and R9 are hydrogen atoms at the same time is excluded.

* * * * *

UNITED STATES PATENT AND TRADEMARK OFFICE
CERTIFICATE OF CORRECTION

| | | |
|---|---|---|
| PATENT NO. | : 7,759,030 B2 | Page 1 of 1 |
| APPLICATION NO. | : 12/569012 | |
| DATED | : July 20, 2010 | |
| INVENTOR(S) | : Abe et al. | |

It is certified that error appears in the above-identified patent and that said Letters Patent is hereby corrected as shown below:

On the title page, Item (30), the Foreign Application Priority Data has been omitted. Item (30) should read:

-- (30)     Foreign Application Priority Data

May 25, 2004     (JP)................................2004-154722 --

Signed and Sealed this
Twenty-fourth Day of May, 2011

David J. Kappos
*Director of the United States Patent and Trademark Office*